US008710095B2

(12) United States Patent
Hausheer

(10) Patent No.: US 8,710,095 B2
(45) Date of Patent: *Apr. 29, 2014

(54) DRUGS FOR PROPHYLAXIS OR MITIGATION OF TAXANE-INDUCED NEUROTOXICITY

(75) Inventor: Frederick H. Hausheer, Boerne, TX (US)

(73) Assignee: Bionumerik Pharmaceuticals, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/135,975

(22) Filed: Apr. 30, 2002

(65) Prior Publication Data

US 2003/0203960 A1 Oct. 30, 2003

(51) Int. Cl.
*A01N 43/02* (2006.01)
*A61K 31/335* (2006.01)
*A01N 41/02* (2006.01)
*A61K 31/255* (2006.01)

(52) U.S. Cl.
USPC .......................... 514/449; 514/517; 424/649

(58) Field of Classification Search
USPC ................ 514/449, 578, 517; 424/649
See application file for complete search history.

(56) References Cited

U.S. PATENT DOCUMENTS

| | | | |
|---|---|---|---|
| 5,789,000 A * | 8/1998 | Hausheer et al. ............ 424/649 |
| 5,808,140 A | 9/1998 | Haridas | |
| 5,808,160 A | 9/1998 | Ruhl et al. | |
| 5,866,169 A * | 2/1999 | Hausheer et al. ............ 424/469 |
| 5,866,615 A * | 2/1999 | Hausheer et al. ............ 514/707 |
| 5,866,617 A | 2/1999 | Hausheer et al. | |
| 5,902,610 A * | 5/1999 | Hausheer et al. ............ 424/649 |
| 5,919,816 A * | 7/1999 | Hausheer et al. ............ 514/449 |
| 5,922,902 A | 7/1999 | Haridas | |
| 5,998,479 A | 12/1999 | Hausheer | |
| 6,025,488 A * | 2/2000 | Hausheer ..................... 540/454 |
| 6,031,006 A | 2/2000 | Hausheer et al. | |
| 6,034,126 A | 3/2000 | Hausheer | |
| 6,037,336 A | 3/2000 | Hausheer et al. | |
| 6,040,294 A | 3/2000 | Hausheer et al. | |
| 6,040,304 A | 3/2000 | Hausheer et al. | |
| 6,040,312 A | 3/2000 | Hausheer et al. | |
| 6,043,249 A | 3/2000 | Hausheer et al. | |
| 6,043,274 A | 3/2000 | Hausheer et al. | |
| 6,046,159 A | 4/2000 | Hausheer et al. | |
| 6,046,234 A | 4/2000 | Hausheer et al. | |
| 6,048,849 A | 4/2000 | Hausheer et al. | |
| 6,057,361 A | 5/2000 | Hausheer et al. | |
| 6,066,645 A | 5/2000 | Hausheer et al. | |
| 6,066,668 A | 5/2000 | Hausheer et al. | |
| 6,075,053 A | 6/2000 | Hausheer | |
| 6,077,838 A | 6/2000 | Hausheer | |
| 6,100,247 A | 8/2000 | Hausheer et al. | |
| 6,143,796 A | 11/2000 | Hausheer | |
| 6,172,119 B1 | 1/2001 | Hausheer | |
| 6,177,411 B1 | 1/2001 | Hausheer | |
| 6,197,831 B1 | 3/2001 | Hausheer | |
| 6,225,295 B1 | 5/2001 | Hausheer et al. | |
| 6,245,815 B1 | 6/2001 | Peddaiahgari | |
| 6,251,881 B1 | 6/2001 | Hausheer et al. | |
| 6,255,355 B1 | 7/2001 | Peddaiahgari | |
| 6,274,622 B1 | 8/2001 | Hausheer et al. | |
| 6,291,441 B1 | 9/2001 | Hausheer et al. | |
| 6,352,979 B1 | 3/2002 | Lizcano | |
| 6,468,963 B1 | 10/2002 | Hausheer et al. | |
| 6,468,993 B1 | 10/2002 | Hausheer | |
| 6,504,049 B1 | 1/2003 | Kochat | |
| 6,525,037 B1 | 2/2003 | Hausheer et al. | |
| 6,596,320 B1 * | 7/2003 | Hausheer ..................... 424/649 |
| 2003/0092681 A1 | 5/2003 | Hausheer | |
| 2003/0133994 A1 | 7/2003 | Hausheer | |
| 2004/0024246 A1 | 2/2004 | Cazaux et al. | |
| 2004/0152774 A1 | 8/2004 | Hausheer | |
| 2005/0137419 A1 | 6/2005 | Kawami et al. | |

FOREIGN PATENT DOCUMENTS

| | | | |
|---|---|---|---|
| JP | 10-509143 A | | 9/1998 |
| JP | 2001-500872 A | | 1/2001 |
| JP | 2001-501219 A | | 1/2001 |
| WO | WO 93/10076 | * | 5/1993 |
| WO | 9614852 A1 | | 5/1996 |
| WO | 9811898 A1 | | 3/1998 |
| WO | 9814426 A1 | | 4/1998 |
| WO | WO 99/20264 A1 | | 4/1999 |
| WO | 0012469 A1 | | 3/2000 |
| WO | 02056755 A2 | | 7/2002 |
| WO | WO 02056755 | * | 7/2002 |
| WO | 03093226 A1 | | 11/2003 |
| WO | 2004058274 A1 | | 7/2004 |
| WO | 2004084909 A1 | | 10/2004 |

OTHER PUBLICATIONS

Boven et al., European Journal of Cancer 38, (May 2002), pp. 1148-1156.*
Cerny et al. Annals of oncology 10; 1087-1094 (1999).*

(Continued)

*Primary Examiner* — Shirley V Gembeh

(57) ABSTRACT

Provided are pharmaceutical drugs for preventing or mitigating adverse actions associated with taxane antineoplastic drugs which are frequently and widely used in cancer chemotherapy, and pharmaceutical compositions which allow us to shorten the duration of treatment with taxane antineoplastic agents and/or to repeat the taxane treatment course more times, as well as drugs suitable for the therapeutic schedules.

51 Claims, No Drawings

(56) References Cited

OTHER PUBLICATIONS

Abstract: Masudo N, et al; Phase I and pharmacologic study of BNP7787. a novel chemoprotector in patients with advanced non-small cell: Cancer Chemother Pharmacol. May 15, 2010.
Abstract: Parker AR et al; BNP7787-mediated modulation of paciltaxel- and cisplatin-induced aberrant microtubule protein polymerization in vitro. Mol Cancer THer. Sep. 9, 2010(9), 2558-67.
Verschraagen M. et al., "Possible (enzymatic) routes and biological sites for metabolic reduction of BN7787, a new protector against cisplatin-induced side-effects", Biocham Pharmacol, Aug. 1, 2004, 68 (3): 493-502.
Verschraagen M. et al., "Pharmacokinetic behavior of the chemoprotectants BN7787 and mesna after an i.v. bolus injection in rats", Br J Cancer, Apr. 19, 2004; 90 (8) : 1654-9.
Verscharaagen M. et al, "Pharmacokinetics and preliminary clinical data of the novel chemoprotectant BNP7787 and cisplatin and their metabolites", Clin Pharmacol Ther., Aug. 2003; 74 (2); 157-69.
Hausheer FH et al., "New approaches to drug discovery and development; a mechanism-based approach to pharmaceutical research and its application to BNP7787, a novel chemoprotective agent" Cancer Chemother Pharmacol. Jul. 2003; 52 Suppl 1: S3-15. Epub Jun. 18, 2003.
Verschraagen M. et al., "Pharmacokinetics of BNP7787 and its metabolite mesna in plasma and ascites: a case report" Cancer Chemother Pharmacol. Jun. 2003; 51 (6); 525-9. Epub May 15, 2003.
Verschraagen M. et al."The chemical reactivity of BNP7787 and its metabolite mesna with the cytostatic agent cisplatin: comparison with the nucleophiles thiosulfate, DDTC, glutathione and its disulfide GSSG", Cancer Chemother Pharmacol. Jun. 2003; 51 (6); 499-504. Epub Apr. 25, 2003.
Pedyala L. et al., "Modulation of plasma thiols and mixed disulfides by BNP7787 inpatients receiving paclitazel/cisplatin therapy", Cancer Chemother Pharmacol. May 2003; 51 (5); 376-84. Epub Apr. 8, 2003.
Boven E. et al. "BNP7787, a novel protector against platinum-related toxicities, does not affect the efficacy of cisplatin or carboplatin in human tumour xenografts", Eur J Cancer. May 2002; 38 (8); 1148-56.
Hausheer FH et al., "Modulation of platinum-induced toxicities and therapeutic index: mechanistic insights and first- and second-generation protecting agents", Semin Oncol. Oct. 1998; 25 (5); 584-99.
"Clinical Development Summary of N7787", pp. 36-39 of Form S-1 registration statement under the securities act of 1933 as filed with the securities and exchange commission on Mar. 2, 2001 registration No. 333, filed by Bionumerik Pharmaceuticals, Inc. before the Securities and Exchange Commission Washington, D.C. 20549.
Hausheer, F. et al., "BNP7787 Administration in vivo results in increased therapeutic index and toxicity reduction of platinum drugs", Proceedings of the American Association of Cancer Research,vol. 39, Mar. 1998.
Hausheer, F. et al., "BNP7787: A novel antitumor potentiating drug which protects against cisplatin and carboplatin toxicities", Proceedings of the American Association for Cancer Research, vol. 38, Mar. 1997.
Hausheer, F. et al., "Oral and intravenous BNP7787 protects against platinum neurotoxicity without in vitro or in vivo tumor protection", Proceedings of the American Association for Cancer Research, vol. 40, Mar. 1999.
Hausheer F. et al., "Modulation of Platinum-Induced Toxicities and Therapeutic Index: Mechanistic Insights and First- and Second-Generation Protecting Agents", Seminars in Oncology, vol. 25, No. 5 Oct. 1998; pp. 584-599.
Takeda, K. et al., "Phase I safety and pharmacokinetic trial of BNP7787 in patients receiving cisplatin (CDDP) and paclitael (PTX) for advanced non-small cell lung cancer (NSCLC): an Osaka phase I study group trial", Proceedings of the ASCO, vol. 21, 2002.
Hausheer F. et al., "Pharmacokinetics of BNP7787 (dimesna) and its metabolite mesna in plasma and ascites", Proceedings of the $11^{th}$ NCI—EORTC—AACR Symposium, Copyright (c) 2000 Stichting NCI—RORTC Symposium on New Drugs in Cancer Therapy Published by the AACR, 346.
Boven E. et al., "Phase I dose-finding and pharmacokinetics (PK) study of BNP7787 (dimesna) as possible protector of cisplatin-induced side-effects", Annals of Oncology, vol. 11, 2000, Supplement 4, Oct. 25, 2000.
Schwartz G. et al., "Phase I trial of Escalating Doses of BNP7787 in Patients Receiving Paclitaxel (TAX) and Cisplatin (CDDP)", 2000 ASCO Annual Meeting, Abstract No. 849.
Hausheer F. et al., "BNP7787: A novel chemopreotecting agent for Platinum and taxane toxicity", Proceedings of the American Association for Cancer Research, vol. 41, Mar. 2000.
Boven E. et al, "BNP7787 (DIMESNA) as a possible protector of cisplatin-induced toxicities: a dose-finding and pharmacokinetic study" Meeting abstract 646, 1999 ASCO Annual Meeting.
Schilsky R. et al., "Phase I trial of escalating doses on BNP7787 in patients receiving cisplatin (CDDP) and paclitaxel (TAX)", Meeting Abstract 647, 1999 ASCO Annual Meeting.
Phillips, Chemical Modification of Radiation Effects, Cancer 39, pp. 987-999, 1977.
Lemaire et al., The Synthesis of 2-Mercaptoethane-sulfonamide, J. Org. Chem., 26, pp. 1330-1331, (1961).
Brzezinska et al., Syntheses Using 2,2'-Dithiobis(benzothiazole), J. Org Chem., 59, pp. 8239-8244, (1994).
Gordon et al., Phase I Dose Escalation of Paclitaxel in Patients With Advanced Ovarian Cancer Receiving Cisplatin: Rapid Development of Neurotoxicity Is Dose-Limiting, J. Clin. Oncol., 15(5), pp. 1965-1973, 1997.
Hausheer et al., BNP7787: A novel neuroprotective agent in taxane and platinum regimens does not interfere with chemotherapeutic effects, AACR, Abstract #1990, 2001.
Takeda et al, Phase 1 safety and pharmacokinetic trail of BNP7787 in patients receiving cisplatin (CDDP) and paclitaxel (PTX) for advanced non-small cell lung cancer (NSCLC), an Osaka phase 1 study group trial, ASCO. Abstract # 453, 2002.
Takeda et al., Poster Presentation: Phase 1 safety and pharmacokinetic trial of BNP7787 in patients receiving cisplatin (CDDP) and paclitaxel (PTX) for advanced non-small cell lung cancer (NSCLC):, ASCO. Abstract # 453, 2002.
Uejima et al., Phase 1 and pharmacokinetic trial of BNP7787 in patients receiving cisplatin and paclitaxel for advanced Non-Small Cell Lung Cancer (NSCLC), Abstract # 146, 2002.

* cited by examiner

DRUGS FOR PROPHYLAXIS OR MITIGATION OF TAXANE-INDUCED NEUROTOXICITY

FIELD OF THE INVENTION

The present invention relates to drugs that are useful for prophylaxis and mitigation of taxane-induced disorders of peripheral nervous systems, and pharmaceutical compositions for increasing the dosage and/or shortening the duration or schedule of treatment with taxane antineoplastic agents.

BACKGROUND OF THE INVENTION

Many anticancer agents used in chemotherapy are known to cause various undesirable toxicities associated with their cytotoxic properties. It is widely known that there are many instances where such undesirable or intolerable drug related toxicities impose crucial limitations on the dose and schedule for administration of such antineoplastic agents to patients with cancer. It is notable to consider that the drug induced toxicity associated with many cancer chemotherapy drugs can offset the potential benefit to the patient undergoing treatment since the development of chemotherapy induced toxicity can result in delaying treatment, or in severe cases, lead to the discontinuance of treatment altogether. These two outcomes can allow the patient's cancer to progress unchecked or to limit the opportunity to cure or significantly palliate the patient's disease by limiting the dose, duration or schedule of chemotherapy treatments that are aimed at curing or palliating the patient's cancer.

It is well known that such antineoplastic agent-induced toxicities vary with antineoplastic agent species or class that are well recognized by experts. Furthermore, adverse events or toxicities produced by such anticancer drugs are based on a diversity of biochemical and pharmacological mechanisms that may be entirely different from one another even though superficially, the patient's symptoms and signs are apparently identical or similar in terms of the nature of their description. Therefore, it is also known that it is not necessarily a reasonable expectation to prevent or to mitigate all such undesirable toxicities associated with all chemotherapy agents or to inhibit their side effects non-selectively. Drug related side effects occur in vivo upon administration of a specific antineoplastic agent based on the toxicities common to that antineoplastic agent, and observed patient side-effect symptoms vary according to diverse factors and sensitive natures per in vivo tissue, cell or organ and the interaction with other drugs that are administered. Accordingly, the safe and effective means for solving such problems will vary. Of course, it is important to recognize that an ideal chemoprotective agent is one that would not result in an additional separate or additive toxicity to the patient in conjunction with the administration of chemotherapy; this is one of the novel objects of the current invention.

Representatives of taxane antineoplastic agents are paclitaxel, docetaxel, and others currently in clinical and preclinical development. Such taxane antineoplastic agents have been frequently and widely employed to treat patients with breast cancer as well as patients with ovarian, lung, bladder, esophagus, and other sites of origin in the United States, Europe Japan and other countries. However, the administration of taxanes requires precautions because serious and potentially life threatening side effects often occur. In particular, the clinical use of taxanes is frequently delayed or discontinued altogether due to toxicities causing the disorder of peripheral nerve systems (including peripheral neuropathy) such as numbness in the extremities, paresthesias, weakness, paralysis, arthralgia, myalgia, as well as others. In these instances the taxane medication treatment must be suspended, the dose of taxane chemotherapy reduced, or in the more severe cases, it is discontinued because of the neurotoxicity. Halting treatment or altering the dosage of the taxane may be detrimental to the patient's chances of long term survival or control of the cancer, since it is well known that the delay, reduction in dose or the discontinuance of chemotherapy allows the unopposed progression of the patient's cancer. Therefore, a safe and effective solution for preventing or reducing the likelihood of such common and clinically important problems relating to chemotherapy induced neurotoxicity is eagerly demanded since it is estimated that approximately 60% of patients receiving taxane chemotherapy can develop drug induced neurotoxicity.

Up to the present, various attempts have been attempted to mitigate, but not prevent the toxicities of antineoplastic agents. It is notable that there is no currently approved drug therapy that has been demonstrated in patients to be safe and effective in preventing taxane induced neurotoxicity. The treating physician basically has three treatment options: 1) delay treatment until the toxicity resolves to an acceptable level; 2) reduce the dose of taxane chemotherapy; and 3) discontinue treatment with the taxane altogether. The treating physician can employ any combination of 1 and 2 together and option 3 is reserved for more severe cases of taxane neurotoxicity. A variety of new approaches to prevent or mitigate taxane-induced neurotoxicity have been pursued more recently.

Representatives of platinum analogue antineoplastic drugs include cisplatin, carboplatin, oxaliplatin, and others in both clinical and preclinical development. Like the taxanes and many other antineoplastic drugs, platinum analogue antineoplastic drugs are associated with a number of toxicities, including nephrotoxicity, bone marrow suppression, neurotoxicity, and others.

The present inventors have filed patent applications disclosing the use of 2,2'-dithiobis ethane sulfonate and other dithioethers in order to alleviate cisplatin induced toxicity, i.e., nephrotoxicity (U.S. Pat. Nos. 5,789,000; 5,866,169; 5,866,615; 5,866,617; 5,902,610 and others . . . JP, A, 10-509143 (1998)) and carboplatin induced toxicity, i.e., myelosuppression, and also vomiting (U.S. Pat. No. 6,037,336; JP, A, 2001-500872 (2001)). The present inventors have also pointed out that 2,2'-dithiobis ethane sulfonate and dithioethers are applicable to mitigation of toxicities mediated by various antineoplastic agents (U.S. Pat. Nos. 5,919,816; 6,025,488; 6,040,294; 6,040,304; 6,040,312; 6,043,249; 6,046,159; 6,046,234; 6,048,849; 6,057,361; 6,066,645; and 6,066,668; WO 99/20264).

In the above WO 99/20264 and U.S. Pat. No. 5,919,816, a very broad range is disclosed for dose rates of dithioethers to taxane antineoplastic agents, i.e., the weight-to-weight ratio of taxane antineoplastic agent to dithioethers is from 1:4 to 1:4,000 for parenteral administration routes; however, with regard to dithioethers, the optimum dosage for use in humans has not been fully determined and is expected to be highly variable because of the wide variability of doses and schedules of chemotherapy agents that are used alone and in combination with different treatment regimens for cancer patients.

The process for synthesizing the dithioethers is outlined in U.S. Pat. No. 5,808,160 and others.

SUMMARY OF THE INVENTION

Under such circumstances, the present inventors have carried out an intensive study for 2,2'-dithiobis ethane sulfonate among the dithioethers. As a result, the present inventors have discovered that pharmaceutical preparations comprising 2,2'-dithiobis ethane sulfonate, also known as dimesna and/or BNP7787, (either as the disodium salt or as a free acid) particularly certain dosages of 2,2'-dithiobis ethane sulfonate, allow for (1) the substantially safe and effective prevention as well as mitigation of the aforementioned taxane antineoplastic agent related neurotoxicity, in particular, paresthesias in peripheral nerve systems; (2) the more effective duration of treatment with taxane antineoplastic agents by preventing treatment delays, taxane dosage reductions and discontinuance of chemotherapy secondary to neurotoxicity; and (3) this invention allows the safe and effective administration of many more than the average number of cycles of antineoplastic drug medication than previously possible. As a result of our research we also believe that it will be possible to increase the dosage of chemotherapy as well without additional toxicity and that this may result in substantially improved patient benefit from such treatment. The evidence of patient benefit from this present invention is clearly manifested by two patients who would not be expected to experience a complete disappearance of their cancer (one of these patients has a probable metastatic non-small cell lung cancer to the brain and has been in a complete remission for more than one year and the other patient has a cholangiocarcinoma that has undergone complete remission in less than 3 months of taxane based chemotherapy. In addition, many other patients receiving this novel chemoprotectant in combination with taxane-based chemotherapy have experienced major antitumor responses that have lasted for months. None of any of these patients has experienced severe taxane induced neurotoxicity, including patients who have received up to 9 chemotherapy cycles of treatment. Based on further investigation, the inventors have succeeded in completing the present invention.

The present invention relates to effective amounts of dithioether drugs for preventing or mitigating taxane antineoplastic agent-induced neurotoxicity, more specifically the taxane antineoplastic agent-induced toxic paresthetic disorder of peripheral nerve systems.

The present invention relates to disulfide chemoprotectant admixed pharmaceutical compositions and drugs for coadministration with taxane antineoplastic agents which enable us to shorten the duration of treatment with taxane antineoplastic agents, and/or to repeat the taxane antineoplastic agent medication course more times than ever. This invention also teaches a new and useful method to prevent taxane treatment delays, treatment discontinuance, and to allow chemotherapy dose increases as well as to shorten the infusional/administration time for patients.

The present invention further relates to disulfide containing chemoprotective agents that are administered as mixtures or in combination with taxane chemotherapy agents for the purpose of preventing taxane agent-induced disorders and toxicity to the peripheral nerve systems, more specifically the taxane antineoplastic agent-induced sensory and motor disorders of peripheral nerve systems. The present invention also involves the co-formulation or co-administration of disulfide containing chemoprotective drugs in combination with taxane drugs which allow the physician to prevent or reduce the probability of taxane treatment delays, taxane dose reductions, discontinuance of taxane chemotherapy, and also to permit the physician to shorten the infusional time for taxane treatment with said antineoplastic agents, and/or to increase the dose of the antineoplastic agent and/or to repeat the antineoplastic agent medication course more times, in connection with not only taxanes alone but also in combination with platinum analogue antineoplastic drug coadministration therapy. All of these benefits relate to the prevention or mitigation of taxane-induced neurotoxicity by this invention as well as to allow more aggressive chemotherapy treatment to be given without greater toxicity to the patient.

The present invention also relates to 2,2'-dithiobis ethane sulfonate-admixed pharmaceutical compositions and drugs, which enable the physician to safely and effectively co-administer taxane antineoplastic agents in combination with platinum analogue antineoplastic agents, prevent or reduce the probability of taxane treatment delays, taxane dose reductions, discontinuance of taxane chemotherapy to shorten the duration of treatment with said antineoplastic agents, and/or to increase the dose of the antineoplastic agent and/or to repeat the antineoplastic agent medication course more times. All of the foregoing benefits relate to the prevention or mitigation of taxane and platinum induced neurotoxicity by this invention.

The present invention also relates to drugs for preventing or mitigating the taxane antineoplastic agent-mediated disorder of peripheral nerve systems, more specifically the taxane antineoplastic agent-mediated sensory and/or motor disorders of peripheral nerve systems, which contain 2,2'-dithiobis ethane sulfonate or a disulfide at a specific admixture amount per total pharmaceutical preparation.

The present invention also relates to novel pharmaceutical compositions and drugs for coadministration with taxane antineoplastic agents that contain a specific amount of chemoprotectant and enable the physician to prevent or reduce the probability of taxane treatment delays, taxane dose reductions, discontinuance of taxane chemotherapy resulting from taxane induced neurotoxicity, and to allow the physician to shorten the infusional administration treatment with taxane antineoplastic agents and/or to safely allow the physician and patient to receive more courses of chemotherapy as well as to allow dose escalation of chemotherapy that would otherwise not be achievable without the use of the instant invention. The present invention further relates to drugs which comprise a specific amount of disulfide chemoprotectant and to prevent or mitigate the taxane antineoplastic agent-induced disorder of peripheral nerve systems, more specifically the taxane antineoplastic agent-induced sensory or motor disorder of peripheral nerve systems, and/or drugs which comprise a specific amount of disulfide chemoprotectant and allow the physician to prevent or reduce the probability of taxane treatment delays, taxane dose reductions, discontinuance of taxane chemotherapy, to shorten the duration of treatment with said antineoplastic agents, and/or to repeat the antineoplastic agent medication treatment for more courses, and/or in higher doses, in connection with not only taxane but also platinum analogue antineoplastic drug coadministration therapy.

The present invention also relates to pharmaceutical compositions and drugs that comprise a specified amount of 2,2'-dithiobis ethane sulfonate and enable us to co-administer taxane antineoplastic agents in combination with platinum analogue antineoplastic agents, to shorten the duration of treatment with said antineoplastic agents, and/or to repeat the antineoplastic agent medication course more times, with possible dose escalation of the antineoplastic agent. The present invention also relates to pharmaceutical preparations wherein the disulfide chemoprotectant is admixed or used together at a specific amount or concentration in solution to 1 part by weight, molar ratio or concentration of taxane antineoplastic agents.

In another aspect, the present invention provides pharmaceutical drugs, pharmaceutical compositions, drug sets, therapeutic measures or methods, therapeutic schedules, packs suitable for taxane antineoplastic therapy (including therapy in combination with platinum analogue antineoplastic drugs), and the like, which comprise disulfide chemoprotectants in any of preferred forms for preventing or mitigating the said taxane antineoplastic agent-related adverse actions in fields of said therapy.

DESCRIPTION OF THE PREFERRED EMBODIMENTS

Specific embodiments of the present invention are listed as follows:

1) a drug for mitigating or preventing taxane antineoplastic agent-induced or -mediated disorder of peripheral nerve systems, which comprises an effective amount of disulfide chemoprotectant;
2) a drug for preventing mitigating the taxane antineoplastic agent-induced sensory or motor disorder of peripheral nerve systems, which comprises an effective amount of disulfide chemotherapy;
   1. administration of a disulfide chemoprotectant that enables the physician to shorten the infusional administration period of taxanes—thereby allowing for greater patient convenience and lower hospital costs;
   2. administration of a disulfide chemoprotectant that enables the physician to reduce the probability of taxane induced neurotoxicity leading to treatment delays, treatment discontinuance, and to allow higher doses and/or shorter intervals of taxane therapy to be administered to cancer patients.
   3. administration of a disulfide chemoprotectant to a cancer patient with or without mild to moderate neurotoxicity from any cause (diabetes, alcoholic, other drug induced—e.g., ethambutol, dilantin, vincristine, tegretol, epothilone, etc. neuropathies, nutritional neuropathy, and the like, that would allow the affected patient to receive taxane based chemotherapy that would not otherwise be contraindicated due to the presence of a pre-existing neuropathy
3) a drug for shortening the infusion period and or the interval of treatment with a taxane antineoplastic agent in taxane antineoplastic therapy, which comprises an effective amount of 2,2'-dithiobis ethane sulfonate.
4) this may allow administration of chemotherapy to a patient for more than one year.
5) Molar ratios would be BNP7787: taxane of 50:1 to as high as 2000:1.
4) the drug according to the above 3) in which the duration of treatment consists of a specified period for medication of a taxane antineoplastic agent and an interval for suspending taxane antineoplastic agent medication.
5) the drug according to the above 4) in which the duration of treatment comprises at least 3 continuous courses wherein each course consists of a specified period for medication of a taxane antineoplastic agent and an interval for suspending taxane antineoplastic agent medication;
6) a drug for shortening an interval for suspending the medication of a taxane antineoplastic agent (or an interval intervening to next taxane antineoplastic agent medication in order to temporarily halt taxane antineoplastic agent administration) in taxane antineoplastic therapy, which comprises an effective amount of 2,2'-dithiobis ethane sulfonate;
7) the drug according to any of the above 4) to 6) in which the interval for administering the taxane antineoplastic agent medication is from 1 day to 4 weeks;
8) the drug according to any of the above 4) to 6) in which the interval for administering the taxane antineoplastic agent medication is from 1 day to 2 weeks;
9) the drug according to any of the above 4) to 6) in which the interval for administering the taxane antineoplastic agent medication is from 1 day to 1.5 weeks;
10) the drug according to any of the above 4) to 6) in which the interval for administering the taxane antineoplastic agent medication is from 1 day to 1.0 weeks;
11) a drug for increasing the number of courses for treatment with a taxane antineoplastic agent (or a course number wherein each course is comprised of one taxane antineoplastic agent medication period and one interval for administering the taxane antineoplastic agent medication) in taxane antineoplastic therapy, which comprises an effective amount of 2,2'-dithiobis ethane sulfonate;
12) the drug according to the above 111) in which the taxane treatment comprises 2 or more treatment courses;
13) the drug according to the above 11) in which the taxane treatment comprises 5 or more courses;
14) the drug according to the above 11) in which the taxane treatment comprises 6 or more courses;
15) the drug according to the above 11) in which the taxane treatment comprises 7 or more courses;
16) the drug according to the above 11) in which the taxane treatment comprises 8 or more courses;
17) the drug according to the above 11) in which the taxane treatment comprises 9 or more courses;
18) the drug according to any of the above 11) to 17), in which said courses are continuous;
19) a drug for mitigating taxane antineoplastic agent-related adverse actions which comprises plural or all members selected from elements as set forth in any of the above 1) to 18);
20) the drug according to any of the above 1) to 19) in which 2,2'-dithiobis ethane sulfonate is admixed at 5 to 70 wt % per total pharmaceutical preparation;
21) the drug according to any of the above 1) to 19) in which 2,2'-dithiobis ethane sulfonate is admixed at 10 to 50 wt %;
22) the drug according to any of the above 1) to 21) in which the amount of admixed 2,2'-dithiobis ethane sulfonate is for administrating 4.1 g/m$^2$ to 80.0 g/m$^2$ (body surface area) per dose;
23) the drug according to any of the above 1) to 22) which is for intravenous or oral administration routes;
24) the drug according to the above 23) in which the drug for intravenous or oral administration routes is in any of solution or suspension in liquid form, freeze-dried and solid forms;
25) the drug according to any of the above 1) to 24) in which the taxane antineoplastic agent is paclitaxel;
26) the drug according to any of the above 1) to 24) in which the taxane antineoplastic agent is docetaxel;
27) the drug according to any of the above 1) to 26) which is for taxane antineoplastic drug therapy in combination with platinum analogue antineoplastic drug therapy;
28) the drug according to the above 27) in which the platinum analogue antineoplastic agent is cisplatin;
29) the drug according to the above 27) in which the platinum analogue antineoplastic agent is carboplatin;
30) a pharmaceutical composition for coadministration with a taxane antineoplastic agent, which comprises an effective amount of 2,2'-dithiobis ethane sulfonate in order to mitigate the taxane antineoplastic agent-induced disorder of peripheral nerve systems;

31) a pharmaceutical composition for coadministration with a taxane antineoplastic agent, which comprises an effective amount of 2,2'-dithiobis ethane sulfonate in order to mitigate the taxane antineoplastic agent-induced paresthetic disorder of peripheral nerve systems;
32) a pharmaceutical composition for coadministration with a taxane antineoplastic agent, which comprises an effective amount of 2,2'-dithiobis ethane sulfonate in order to shorten the duration of treatment with the taxane antineoplastic agent in taxane antineoplastic therapy;
33) a pharmaceutical composition for coadministration with a taxane antineoplastic agent, which comprises an effective amount of 2,2'-dithiobis ethane sulfonate in order to shorten an interval for administering medication with the taxane antineoplastic agent in any taxane containing antineoplastic therapy;
34) a pharmaceutical composition for coadministration with a taxane antineoplastic agent, which comprises an effective amount of 2,2'-dithiobis ethane sulfonate in order to increase the number of courses of treatment with a taxane antineoplastic agent in taxane antineoplastic therapy;
35) a pharmaceutical composition for coadministration with a taxane antineoplastic agent, which comprises an effective amount of 2,2'-dithiobis ethane sulfonate in order to exert plural or all actions selected from the group consisting of
   1. a mitigating activity against the taxane antineoplastic agent-related disorder of peripheral nerve systems,
   2. a mitigating activity against the taxane antineoplastic agent-related paresthetic disorder of peripheral nerve systems,
   3. a shortening of the duration of taxane antineoplastic agent treatment,
   4. a shortened time interval for administering taxane antineoplastic agent medication during taxane antineoplastic drug therapy, and
   5. an increasing activity on the number of courses for taxane antineoplastic agent medication during taxane antineoplastic drug therapy;
36) the pharmaceutical composition according to any of the above 30) to 35) in which 2,2'-dithiobis ethane sulfonate is admixed at 5 to: >70 wt % per total pharmaceutical preparation;
37) the pharmaceutical composition according to any of the above 30) to 35) in which 2,2'-dithiobis ethane sulfonate is admixed at 0.10 to 50 wt %;
38) the pharmaceutical composition according to any of the above 30) to 35) in which the amount of admixed 2,2'-dithiobis ethane sulfonate is for administrating 4.1 to 80.0 g/m$^2$ (body surface area) per dose;
39) the pharmaceutical composition according to any of the above 30) to 38) which is for intravenous or oral administration routes;
40) the pharmaceutical composition according to the above 39) in which the drug for intravenous or oral administration routes is in any of liquid, freeze-dried and solid forms;
41) the pharmaceutical composition according to any of the above 30) to 40) in which the taxane antineoplastic agent is paclitaxel;
42) the pharmaceutical composition according to any of the above 30) to 40) in which the taxane antineoplastic agent is docetaxel;
43) the pharmaceutical composition according to any of the above 30) to 42) which is for taxane antineoplastic drug therapy in combination with platinum analogue antineoplastic drug therapy;
44) the pharmaceutical composition according to the above 43) in which the platinum analogue antineoplastic agent is cisplatin;
45) the pharmaceutical composition according to the above 43) in which the platinum analogue antineoplastic agent is carboplatin;
46) a drug comprising an effective amount of 2,2'-dithiobis ethane sulfonate for coadministration with a taxane antineoplastic agent in a form of packs or formulations in order to allow the following:
   (1) one course is set to include the following administration schedules: the taxane antineoplastic agent is administered once a day wherein the antineoplastic agent is administered at 1 day to 5 week intervals, and 2,2'-dithiobis ethane sulfonate is administered on the same date as the antineoplastic agent is administered, and
   (2) the medication is repeated for at least 4 courses, preferably 7 or more courses;
47) the drug according to the above 46) in which the weight ratio of 2,2'-dithiobis ethane sulfonate to antineoplastic agent is from 1:10 to 1:2500;
48) the drug according to the above 46) in which the dose of 2,2'-dithiobis ethane sulfonate is from 4.1 to 80.0 g/m$^2$ (body surface area);
49) the drug according to any of the above 46.) to 48) in which the single dose of the taxane antineoplastic agent is from 60 to 300 mg/m$^2$ (body surface area) per day for paclitaxel or from 30 to 240 mg/m$^2$ (body surface area) per day for docetaxel;
50) the drug according to any of the above 46) to 49) in which the course is repeated at least 8 or more times;
51) the drug according to any of the above 46) to 50) in which the antineoplastic agents are administered at intervals of (a) one day to 4 weeks, (b) one day to 3 weeks, or (c) one day to 2 weeks;
52) the drug according to any of the above 46) to 50) in which the antineoplastic agent is administered at an interval of one day to 1.5 weeks;
53) the drug according to any of the above 46) to 52) which exerts at least one, plural or all actions selected from the group consisting of
   (1) a mitigating activity against the taxane antineoplastic agent-related disorder of peripheral nerve systems,
   (2) a mitigating activity against the taxane antineoplastic agent-related paresthetic disorder of peripheral nerve systems,
   (3) a shortening activity on the duration of taxane antineoplastic agent treatment,
   (4) a shortening activity on the interval for suspending taxane antineoplastic agent medication during taxane antineoplastic drug therapy, and
   (5) an increasing activity on the number of courses for taxane antineoplastic agent medication during taxane antineoplastic drug therapy;
54) a drug comprising an effective amount, of 2,2'-dithiobis ethane sulfonate for coadministration with a taxane antineoplastic agent in a form of packs or formulations in order to allow the following:
   (1) one course is set to include the following administration schedules:
      the taxane antineoplastic agent is administered once per day as well as a platinum analogue antineoplastic agent is administered on the same date as the taxane antineoplastic agent is administered wherein the antineoplastic agents are administered at one day to 6 week intervals, and 2,2'-dithiobis ethane sulfonate is administered on the same date as the antineoplastic agents are administered, and (2) the medication is repeated for at least 4 courses, preferably 7 or more courses;

55) the drug according to the above 54) in which the weight ratio of 2,2'-dithiobis ethane sulfonate to taxane antineoplastic agent is from 1:10 to 1:2500.

56) the drug according to the above 54) in which the dose of 2,2'-dithiobis ethane sulfonate is from 4.1 to 80.0 g/m² (body surface area);

57) the drug according to any of the above 54) to 56) in which the single dose of the taxane antineoplastic agent is from 60 to 300 mg/m² (body: surface area) per day for paclitaxel or from 30 to 240 mg/m² (body surface area) per day for docetaxel;

58) the drug according to any of the above 54) to 56) in which the platinum analogue antineoplastic agent is cisplatin or carboplatin;

59) the drug according to any of the above 54) to 58) in which the course is repeated at least 8 or more times;

60) the drug according to any 6£ the above 54) to 59) in which the antineoplastic agents are administered at intervals of (a) one day to 5 weeks, (b) one day to 4 weeks or (c) one day to 3 weeks;

61) the drug according to any of the above 54) to 59) in which the antineoplastic agent is administered at an interval of 2.5 to 5 weeks;

62) the drug according to any of the above 54) to 61) which exerts at least one, plural or all actions selected from the group consisting of
  (1) a mitigating activity against the taxane antineoplastic agent-related disorder of peripheral nerve system,
  (2) a mitigating activity against the taxane antineoplastic agent-related paresthetic disorder of peripheral nerve system,
  (3) a shortening activity on the duration of taxane antineoplastic agent treatment,
  (4) a shortening activity on the interval for suspending taxane antineoplastic agent medication during taxane antineoplastic drug therapy, and
  (5) an increasing activity 63) the drug according to any of the above 46) to 62) which serves as an agent for mitigating taxane antineoplastic agent-related adverse actions;

64) the pharmaceutical composition according to any of the above 30) to 45) in which 2,2'-dithiobis ethane sulfonate is co-administrable as a medication set in combination with taxane antineoplastic agent medication;

65) the pharmaceutical composition according to 64) in which a platinum analogue antineoplastic agent is co-administrable as a medication set; and The aforementioned taxane antineoplastic agent includes paclitaxel, docetaxel and derivatives and analogues thereof. Among them, paclitaxel and docetaxel have been already approved and marketed as pharmaceutical drugs, and other taxanes are in clinical and preclinical development.

The aforementioned platinum analogue antineoplastic agents include cisplatin, carboplatin and other platinum derivatives. Among them, cisplatin and carboplatin have been already approved and marketed as pharmaceutical drugs, and other platinum agents are in various stages of clinical and preclinical development.

The aforementioned 2,2'-dithiobis ethane sulfonate is a known compound, J. Org. Chem., 26, 1330 (1961); J. Org. Chem., 59, 8239 (1994); etc., and can be manufactured by methods as described in those known documents or according to techniques similar thereto or as described in the U.S. Patents referred to, supra. Alternatively, 2,2'-dithiobis ethane sulfonate can also manufactured by a method disclosed in JP, A, 2001-501219 (2001).

The present invention provides pharmaceutical drug for preventing or mitigating the taxane anticancer drug-related disorder of peripheral nerve systems (including peripheral neuropathy), which comprises an effective amount of 2,2'-dithiobis ethane sulfonate. Particularly, the present invention provides embodiments for a pharmaceutical drug for preventing or mitigating the taxane anticancer drug-related paresthetic disorder of peripheral nerve systems (including peripheral neuropathic paresthesia) in relation to taxane drug therapy, which comprises an effective amount of 2,2'-dithiobis ethane sulfonate.

In an embodiment, the present invention provides a drug for mitigating the taxane anticancer drug-related disorder of peripheral nerve systems which contains 2,2'-dithiobis ethane sulfonate at a dose of a specific wt %. The percent amount of admixed 2,2'-dithiobis ethane sulfonate is preferably from 5% to 70 wt %, and more, preferably from 10% to 50 wt % per total pharmaceutical preparation.

When a taxane antineoplastic agent is administered, the disorder of peripheral nerve systems (e.g., peripheral neuropathy) is said to most frequently occur as an adverse effect and its onset rate is more than 60% in patients who receive taxane based chemotherapy. The taxane antineoplastic agent-related disorder of peripheral nerve systems (e.g., peripheral neuropathy) may include main symptoms such as paresthesia (an abnormal sensation, such as numbness, tingling, burning, distal anesthesia, etc.) in relation to the limbs. The drug for mitigating the taxane anticancer drug-mediated disorder can prevent or alleviate such disorders of peripheral nerve systems, including numbness, pain and the like in the limbs.

The mitigating and suppressing (or inhibiting) efficacy of 2,2'-dithiobis ethane sulfonate on the aforementioned taxane antineoplastic agent-mediated disorder of peripheral nerve systems is supported by Examples, which are set forth below.

The dosage forms of the aforementioned drugs or pharmaceutical compositions are not limited to, but include any as long as they are suitable for achieving the objectives of the present invention. Dosage is preferably by intravenous or oral administration route.

Thus, a taxane antineoplastic agent may be usually administered intravenously while the inventive drugs and pharmaceutical compositions may be in any of dosage forms, i.e., intravenous formulations wherein the administration route is identical with that for the taxane antineoplastic agent or oral formulations wherein the administration route is different from a taxane dosage route.

The above-mentioned drugs or pharmaceutical compositions for intravenous or oral administration routes may be in any of liquid, freeze-dried and solid forms as mentioned below. Usually, each dosage form as aforementioned can be manufactured by admixing 2,2'-dithiobis ethane sulfonate with one or more members selected from pharmaceutically acceptable additives (hereinafter also referred to "pharmaceutical ingredients).

For example, the intravenous formulation contains one or more members selected from pharmaceutical ingredients suitable for liquid or freeze-dried formulations. The additives include pharmaceutical ingredients suitable for aqueous or non-aqueous injections. Usually, the additive is selected from conventional pharmaceutical ingredients such as solubilizers, solution adjuvants, suspending agents, buffers (pH regulators), stabilizers and preservatives. In addition, it may be selected from conventional ingredients suitable for preparation of powders for injection, which are used in solution or suspension when administered.

The oral formulation contains one or more members selected from pharmaceutical ingredients suitable for liquid, freeze-dried and solid formulations. The additives are any pharmaceutical ingredients as long as they are suitable for oral drugs and the intended purposes according to the present invention. Usually, the pharmaceutical additive is selected from conventional pharmaceutical ingredients such as vehicles, binders, disintegrants, lubricants and coating agents. The oral formulations of the present invention include solid and liquid forms. The solid oral preparations include tablets, capsules, granules, fine granules, powders, etc. The liquid oral preparations include syrups, etc.

Next, the present invention provides pharmaceutical compositions for coadministration with a taxane antineoplastic agent which comprise an effective amount of 2,2'-dithiobis ethane sulfonate to shorten the duration of treatment with the taxane antineoplastic agent. In a more specific embodiment, the present invention provides pharmaceutical compositions for coadministration with a taxane antineoplastic agent which comprise 2,2'-dithiobis ethane sulfonate at a specific wt % to shorten.

The amount ratio of admixed 2,2'-dithiobis ethane sulfonate in the drug or pharmaceutical composition of the present invention is preferably from 5 to 70 wt %, or more preferably from 10 to 50 wt %.

Coadministration of the instant drug or pharmaceutical composition in combination with a taxane antineoplastic agent enables us to shorten the duration of taxane antineoplastic agent treatment, though it has been deemed clinically difficult to shorten the duration of taxane treatment because of its safety.

Thus, when a taxane antineoplastic agent is applied to cancer therapy, it is usually administered once a day. The daily dose for paclitaxel is around 60 to 300 mg/m$^2$ (body surface area) and for docetaxel around 30 to 240 mg/m$^2$ (body surface area).

Currently, a taxane antineoplastic agent is administered at the above dose once a day and taxane antineoplastic agent medication then halts for at least 3 to 4 weeks, wherein this medication schedule is set as one course and the course is repeated for cancer therapy (for example, it is noted that the following dosage and administration instructions are present in a approved prescription for paclitaxel injection (TAXOL Injection, Japan):

Paclitaxel can be infused intravenously over 3 hours at 210 mg/m$^2$ (body surface area) once a day followed by halting paclitaxel medication for at least 3 weeks wherein this is defined as one course and the course should be repeated.

In view of these, the duration of treatment with the said taxane antineoplastic agents will be equal to a long period. For achieving a clinical effect in taxane antineoplastic drug therapy, it is said to be necessary that taxane antineoplastic agent medication should be repeated continuously for at least 2 courses. However, frequently induced disorders of peripheral nerve system (including peripheral neuropathy) often bring taxane antineoplastic agent medication to a halt or lead to a reduced dose whereby it sometimes happens that the expected clinical effect is not so easily achieved.

When the inventive drugs and pharmaceutical compositions wherein 2,2'-dithiobis ethane sulfonate is contained at the specific parts by weight as aforementioned are coadministered in combination with taxane antineoplastic agents, the drug-induced disorder of peripheral nerve systems (including peripheral neuropathy), particularly the drug-induced paresthetic disorder of peripheral nerve systems, can be alleviated so that it would be possible to maintain patients in a good systemic state. Accordingly, taxane antineoplastic agents can be administered as a next course only after an around one day to 2 week interval, or further only after an interval of about one day to 2 week interval, for suspending drug medication, shorter than the aforementioned conventional 3 to 4 week interval for administering drug medication whereby the duration of taxane treatment can be shortened.

In such a case, the dose of taxane antineoplastic agents may be in such a level that the anti-tumor effect can be exerted. In other words, it may be less than the aforementioned single: dose level for paclitaxel and docetaxel. More specifically, paclitaxel may be administered at a single dose of around 60 to 300 mg/m$^2$ (body surface area) per administration and docetaxel at a single dose of around 30 to 240 mg/m$^2$ (body surface area) per administration.

The interval for administering anticancer drug medication is shortened to around one day to 1.5 weeks, or around, one day to 1 week. As a result, it will be possible to shorten an interval for suspending anticancer drug medication.

Even when the abovementioned 3 to 4 week interval for suspending anticancer drug medication is adopted, the inventive drugs and pharmaceutical compositions still allow us to continue taxane antineoplastic medication for a longer period exceeding 3 courses minimally required for the achievement of their clinical effect. For the long-term taxane antineoplastic therapy, the course may be repeated at least 4 or more times, or at least 5 or more times, in other cases, at least 6 or more times, and further 7 to 9 times or more.

These are also supported by the results of the following clinical trials carried out by the present inventors. Thus, as will be mentioned below in Examples, when 2,2'-dithiobis ethane sulfonate is administered, for example at a dose of 8.2 g/m$^2$, to patients to whom two species of antineoplastic agents, i.e., paclitaxel and cisplatin, are coadministered, to our surprise, the course can be now repeated up to 9 times. This is far above the assumption under the present circumstance where there is a report that coadministration of paclitaxel with cisplatin tends to increase the neurotoxicity (*J. Clin. Oncol.*, 15(5), 1965, 1997).

Thus, the present invention also provides drugs for preventing or mitigating taxane anticancer drug-induced disorder of peripheral nerve systems in taxane antineoplastic therapy in combination with platinum analogue antineoplastic therapy which comprises an effective amount of 2,2'-dithiobis ethane sulfonate. In a more specific embodiment, the present invention provides drugs for preventing or mitigating taxane anticancer drug-induced paresthetic disorder of peripheral nerve systems in taxane antineoplastic therapy in combination with platinum analogue antineoplastic therapy which comprises an effective amount of 2,2'-dithiobis ethane sulfonate. In the coadministration therapy of taxane anticancer drugs in combination with platinum analogue antineoplastic agents, because of the admixture of 2,2'-dithiobis ethane sulfonate, the inventive drugs and pharmaceutical compositions also serve as agents which shorten the duration of treatment with the said antineoplastic agents or increase medication repeats of the said antineoplastic agents. Accordingly, the present invention still provides therapeutic methods using 2,2'-dithiobis ethane sulfonate having the aforementioned functions, drug sets suitable therefore, and further medication sets and methods suitable for not only schedules regarding the drug dose and medication halt but also long-term taxane antineoplastic therapy.

As such, the above-mentioned 2,2'-dithiobis ethane sulfonate drugs and pharmaceutical compositions allow us to administer taxane antineoplastic agents at shorter intervals than before and therefore are extremely useful in cancer therapy. In addition, even when the conventional dose intervals are adopted, the inventive 2,2'-dithiobis ethane sulfonate drugs and pharmaceutical compositions allow us to administer taxane antineoplastic agents for a longer period in a continuous manner. As a result, the duration of treatment with taxane antineoplastic agents can be shortened.

The drugs for mitigating the disorder of peripheral nerve systems (including peripheral neuropathy) and pharmaceutical compositions containing a specific amount of 2,2'-dithiobis ethane sulfonate can be coadministered substantially with simultaneous taxane antineoplastic agent administration, or their dosing hours can be staggered as long as they may be allowed to coexist in patient's blood. When the dosing hours are staggered, 2,2'-dithiobis ethane sulfonate may be administered either before or after a taxane antineoplastic agent dose. However, it is preferred that the staggered time difference therebetween is within about 2 hours, and more preferably within 1 hour.

Pharmaceutically acceptable packs or drug sets (and/or containers or packages) and kits (administration or therapeutic kits) comprising one or more active agents, pharmaceutical preparations, compositions, drugs or agents useful in therapy, of the present invention, are also valuable. Such packs and kits comprising one or more containers filled with one or more effective ingredients or components for the aforementioned drugs or compositions. Examples of such packs and kits are pharmaceutically acceptable packs or kits suitably directed to cancer therapy. Typically, associated with such a single or plural containers can be a notice (attached document) in the form prescribed by a governmental agency regulating the manufacture, use or sale of pharmaceuticals or biological products, reflecting approval by the agency of the manufacture, use or sale of the product for human administration. These may include packed products, and further constructs which are constituted via adopting suitable dosage steps, etc. so as to achieve more desirable medical therapy including desired cancer therapy and the like.

Human clinical trials have been conducted in the United States, Europe and Japan regarding the safety and efficacy of the agents that make up this invention. These trials are ongoing. The following is a summary of the results obtained from early-stage (Phase 1) trials in the United States and Japan.

In the Phase I study in the United States, human patients in Stage I received the following treatment regimen every 3 weeks: a single dose of paclitaxel (175 mg/m$^2$) administered intravenously over 3 hours, pre-cisplatin saline hydration (1000 mL 0.9% NaCl) for 2 hours, followed immediately by a single dose of 2,2'-dithiobis ethane sulfonate (4.1, 8.2, 12.3, 18.4, 27.6 and 41.0 g/m$^2$, depending on cohort assignment) administered intravenously over 15 or 30 minutes, a single dose of cisplatin (75 mg/m$^2$) administered intravenously over 1 hour and subsequently post-cisplatin saline hydration (500 cc 0.9% NaCl) for 1 hour.

Patients in Stage II received sequentially decreasing pre- and post-cisplatin hydration (Levels A to D: 1000/500, 500/250, 250/250, 0/0 mL 0.9% NaCl) with the following treatment regimen every 3 weeks: a single dose of paclitaxel (175 mg/m$^2$) administered intravenously over 3 hours, pre-cisplatin saline hydration from 2 hours to 30 minutes, immediately followed by a single dose of 2,2'-dithiobis ethane sulfonate (18.4 g/m$^2$) administered intravenously over 15 minutes, a single dose of cisplatin (75 mg/m$^2$) administered intravenously over 1 hour and subsequently post-cisplatin saline hydration for 1 hour to 30 minutes.

A total of 36 patients (22 patients in Stage I and 14 patients in Stage II) with advanced solid tumors have been enrolled and treated in this study at two clinical sites in the United States. A total of 138 treatment courses of BNP7787 with chemotherapy were given to 36 patients giving an average number of 3.8 treatment cycles per patient. A total of 13 patients (36.1%) completed at least five treatment cycles while 5 patients (13.9%) completed at least seven treatment cycles.

In the Phase I study in Japan, patients received the following treatment regimen every 3 weeks: a single dose of paclitaxel (175 mg/m$^2$) administered intravenously over 3 hours, pre-cisplatin saline hydration for 1 hour, immediately followed by a single dose of 2,2'-dithiobis ethane sulfonate (4.1, 8.2, 12.3, 18.4, 27.6 and 41.0 g/m$^2$, depending on cohort assignment) administered intravenously over 30 minutes, a single dose of cisplatin (75 mg/m$^2$) administered intravenously over 1 hour and subsequently post-cisplatin saline hydration for 1.5 hours.

A total of 19 patients with advanced Non-Small Cell Lung Cancer (NSCLC) have been enrolled and treated in this study at four clinical sites in Japan. Each patient was to receive a total of three treatment cycles during this study. A total of 43 treatment courses of 2,2'-dithiobis ethane sulfonate with chemotherapy were given to 19 patients giving an average of 2.3 treatment cycles per patient. A total of 11 patients (57.9%) completed all three treatment cycles while 8 patients (42.1%) discontinued therapy prior to completing the three treatment cycles.

The number and percentage of patients who reported neurotoxicity in the Phase I studies compared with historical control data are summarized on the next page. Severity grades were measured according to NCI-CTC standards.

Incidence of Neurotoxicity in US & Japan Phase I Studies Compared with Historical Control all Doses of 2,2'-dithiobis Ethane Sulfonate (4.1 to 41.0 g/m$^2$)

Number (%) of Patients

| Neurotoxicity Grade[1] (NCI-CTC) | United States (n = 36) | Japan (NSCLC) (n = 19) | Overall (US & Japan) (n = 55) | Historical Control[2] (n = 38) |
|---|---|---|---|---|
| 1 | 8 (22.2) | 13 (68.4) | 21 (38.2) | 11 (29.0) |
| 2 | 8 (22.2) | 1 (5.2) | 9 (16.4) | 8 (21.0) |
| 3 | 0 (0.0) | 0 (0.0) | 0 (0.0) | 7 (18.0) |
| 4 | 0 (0.0) | 0 (0.0) | 0 (0.0) | 1 (3.0) |
| ≥2 | 8 (22.2) | 1 (5.2) | 9 (16.4) | 16 (42.1) |
| Overall | 16 (44.0) | 14 (73.6) | 30 (54.5) | 27 (71.0) |

[1]No Grade 3 or 4 events of neurotoxicity were reported in the Phase I studies.
[2]Treatment regimen = paclitaxel (135 to 175 mg/m2) administered IV over 3 hours followed by cisplatin (75 mg/mphu 2) administered IV over 30 minutes in patients with gynecologic cancer (Connelly et al., Gyn. Onc. 62: 166-168; 1996).

Overall, peripheral neuropathy, such as numbness, paresthesia or tingling, was reported in 54.5% of patients (30 patients, all severities) in the Phase I studies. The majority of neurotoxicity events experienced was mild in severity where 38.2% of patients (21 patients) reported Grade 1 neurotoxicity. A few patients experienced neurotoxicity events that were moderate in severity where 16.4% of patients (9 patients) reported Grade 2 peripheral neuropathy. No patient experienced Grade 3 or 4 neurotoxicity including, patients who received up to 9 cycles of chemotherapy. Notably, peripheral neuropathy was not a dose limiting toxicity when 2,2'-dithiobis ethane sulfonate was administration concurrently with paclitaxel and cisplatin chemotherapy.

Based on historical control data, the expected overall incidence for neurotoxicity is 71.0% and the incidence of moderate to severe (≥Grade 2) neurotoxicity is 42.1%. Results from the Phase I studies showed a marked reduction in both the overall incidence of neurotoxicity and the incidence of moderate to severe (≥Grade 2) neurotoxicity. As can be noted from the table, the overall incidence for neurotoxicity was 54.5% in the Phase I studies compared with 71.0% from historical control data and the incidence for moderate to severe (≥Grade 2) neurotoxicity was 16.4% in the Phase I studies compared with 42.1% from historical control data. The results indicate that the concurrent administration of 2,2'-dithiobis ethane sulfonate with cisplatin and paclitaxel chemotherapy decreases the incidence of neurotoxicity.

The following are examples of the present invention, which are provided only for illustrative purposes, and not to limit the scope of the present invention.

Example 1

Inhibiting Efficacy of 2,2'-dithiobis Ethane Sulfonate Against Paclitaxel-Induced Abnormal Thermoesthesia Methods Paclitaxel was intravenously administered at a dose of 6 mg/kg once daily to female Wistar rats (8 rats per group) (the initial dosage date was defined as day 0). Treatment was repeated five times every other day.

The efficacy of 2,2'-dithiobis ethane sulfonate on the abnormal thermoesthesia occurring in response to the paclitaxel therapy was assessed using, as an index, a latent period for pseudo pain reactions. The pseudo pain reaction related latent period is defined in terms of seconds counting from the initial point at which the rat hind limb was dipped in a hot water bath of 45° C. until the point at which the rat showed an avoidance reflex. Each pseudo pain reaction-related latent period was measured on the day before the initial paclitaxel dosage (day −1, pretreatment), and daily for three days from the next day after the final paclitaxel dosage (from days 9 to 11, post-treatment), i.e., totally four times.

2,2'-dithiobis ethane sulfonate was, dissolved in water for injection to make its concentration 200 mg/ml upon use and the 2,2'-dithiobis ethane sulfonate solution thus prepared was intravenously administered at the dose of 500 mg/kg or 1,000 mg/kg immediately before the paclitaxel administration.

Results

As will be apparent from Table 1, for groups receiving paclitaxel alone, the latent period prior to the initiation of paclitaxel administration (pretreatment) was 9.4±1.0 seconds while the latent periods on days 9, 10 and 11 post-treatment were 18.9±1.4, 19.9±2.2 and 19.4±2.4 seconds, respectively. As compared with the latent periods simultaneously measured with regard to control groups, it is noted that such paclitaxel administration-related latent periods are significantly elongated (p<0.01: student's t-test or Man-Whitney U-test).

In contrast, there was noted a suppressing tendency as a whole for a latent period in groups receiving 500 mg/kg or 1000 mg/kg of 2,2'-dithiobis ethane sulfonate in advance. In groups receiving 1000 mg/kg of 2,2'-dithiobis ethane sulfonate on day 9, significant suppressing effects to elongate the latent period were noted (p<0.05; Dunnet test).

From the results, it is apparent that 2,2'-dithiobis ethane sulfonate mitigates effectively paclitaxel-induced abnormal thermoesthesia.

TABLE 1

| Dose (mg/kg) 2,2'-dithiobis ethane sulfonate/ Paclitaxel | Latent Period (sec) for Thermal Stimuli at 45° C. (Inhibition Rate %) | | | |
|---|---|---|---|---|
| | Pretreatment | Post-Treatment | | |
| | Day-1 | Day 9 | Day 10 | Day 11 |
| PS/Solvent* (Control Groups) | 9.7 ± 1.0 | 9.9 ± 0.9 | 9.9 ± 1.2 | 9.6 ± 0.8 |
| PS/6 (Paclitaxel Alone) | 9.4 ± 1.0 | 18.9 ± 1.4 | 19.9 ± 2.2 | 19.4 ± 2.4 |
| 500/6 | 9.5 ± 0.8 | 17.6 ± 1.5 (17.8) | 18.1 ± 2.2 (18.0) | 17.5 ± 2.2 (19.4) |
| 1,000/6 | 9.7 ± 1.0 | 15.0 ± 1.0 (43.3) | 16.1 ± 2.5 (38.0) | 14.4 ± 1.4 (51.0) |

*Solvent (Cremophor ® EL:Ethanol:PS = 1:1:46)
PS = Physiological Saline

Example 2

A 34-year-old female patient with adenocarcinoma of unknown origin presented with a pituitary mass and supraclavicular and mediastinal lymph nodes. She received the following treatment regimen every 3 weeks: a single dose of paclitaxel (175 mg/m²) administered IV over 3 hours, pre-cisplatin saline hydration (500 mL 0.9% NaCl) for 1 hour, a single dose of BNP7787 (18.4 g/m²) administered IV over 15 minutes, immediately followed by a single dose of cisplatin (75 mg/m²) administered IV over 1 hour and subsequently post-cisplatin saline hydration (250 mL 0.9% NaCl) for 30 minutes. The patient received a total of six cycles of study treatment and experienced peripheral neuropathy (NCI-CTC Grade 2) during Cycles 4 through 6. The patient experienced a complete response after Cycle 2, which was confirmed after Cycles 4 and 6. The patient discontinued study treatment due to the complete response and remained on study for follow-up.

Example 3

A 43-year-old female patient with adenocarcinoma of gastric origin received the following treatment regimen every 3 weeks: a single dose of paclitaxel (175 mg/m²) administered IV over 3 hours, pre-cisplatin saline hydration (500 mL 0.9% NaCl) for 1 hour, a single dose of BNP7787 (18.4 g/m²) administered IV over 15 minutes, immediately followed by a single dose of cisplatin (75 mg/m²) administered IV over 1 hour and subsequently post-cisplatin saline hydration (250 mL 0.9% NaCl) for 30 minutes. The patient received a total of five cycles of study treatment with no peripheral neuropathy. The patient experienced stable disease from Cycles 2 through 4 and was subsequently discontinued from the study due to progressive disease following Cycle 5.

Example 4

A 46-year-old female patient with adenocarcinoma of unknown origin presented with retroperitoneal and lung masses. She received the following treatment regimen every 3 weeks: a single dose of paclitaxel (175 mg/m²) administered IV over 3 hours, pre-cisplatin saline hydration (250 mL 0.9%

NaCl) for 30 minutes, a single dose of BNP7787 (18.4 g/m²) administered IV over 15 minutes, immediately followed by a single dose of cisplatin (75 mg/m²) administered IV over 1 hour and subsequently post-cisplatin saline hydration (250 mL 0.9% NaCl) for 30 minutes. The patient received a total of six cycles of study treatment and experienced Grade 1 numbness and tingling (peripheral neuropathy) beginning Day 2 of Cycle 1 which resolved on Day 5. The patient again experienced Grade 1 peripheral neuropathy during Cycle 4. The patient experienced a partial response after Cycle 2 and a complete response after Cycle 6. The patient discontinued study treatment due to the complete response and remained on study for follow-up.

Example 5

A 69-year-old male patient with adenocarcinoma of the lung received the following treatment regimen every 3 weeks: a single dose of paclitaxel (175 mg/m²) administered IV over 3 hours, pre-cisplatin saline hydration for 1 hour, immediately followed by a single dose of BNP7787 (18.4 g/m²) administered IV over 30 minutes, a single dose of cisplatin (75 mg/m²) administered IV over 1 hour and subsequently post-cisplatin saline hydration for 1.5 hours. The patient received a total of 3 cycles of study treatment and experienced no peripheral neurotoxicity. The patient had a partial response after Cycles 2 and 3 and was discontinued from the study after completing the pre-defined number of treatment cycles.

Example 6

A 52-year-old female patient with adenocarcinoma of the lung received the following treatment regimen every 3 weeks: a single dose of paclitaxel (175 mg/m²) administered IV over 3 hours, pre-cisplatin saline hydration for 1 hour, immediately followed by a single dose of BNP7787 (18.4 g/m²) administered IV over 30 minutes, a single dose of cisplatin (75 mg/m²) administered IV over 1 hour and subsequently post-cisplatin saline hydration for 1.5 hours. The patient received a total of 3 cycles of study treatment and experienced Grade 1 peripheral neurotoxicity beginning on Day 6 of Cycle 3, which resolved on Day 20 of Cycle 3. The patient had a partial response after Cycles 2 and 3 and was discontinued from the study after completing the pre-defined number of treatment cycles.

Example 7

A 53-year-old male patient with large cell carcinoma of the lung received the following treatment regimen every 3 weeks: a single dose of paclitaxel (175 mg/m²) administered IV over 3 hours, pre-cisplatin saline hydration for 1 hour, immediately followed by a single dose of BNP7787 (18.4 g/m²) administered IV over 30 minutes, a single dose of cisplatin (75 mg/m²) administered IV over 1 hour and subsequently post-cisplatin saline hydration for 1.5 hours. The patient received a total of 3 cycles of study treatment and experienced Grade 1 peripheral neurotoxicity beginning on Day 5 of Cycle 2. The patient had stable disease and was discontinued from the study after completing the pre-defined number of treatment cycles.

What is claimed is:

1. A method for treating a patient having breast cancer, ovarian cancer, lung cancer, bladder cancer, or adenocarcinoma, the method, comprising:
   administering a course of therapy to the patient comprising
   a first composition comprising a therapeutically effective amount of an antineoplastic agent and a second composition selected from the group consisting of compositions comprising 2,2'-dithiobis ethane sulfonate in an amount ranging from 4.1 to 41.0 g/m2, 2,2'-dithiobis ethane sulfonate in an amount ranging from 12.3 g/m2 to 27.6 g/m2, and 2,2'-dithiobis ethane sulfonate in an amount of 18.4 g/m2;
   repeating the course of therapy from at least once a day to at least once every 2.5 weeks,
   wherein (a) the amount of antineoplastic agent administered in conjunction with the second composition is greater than the amount administered without the second composition and/or (b) the duration of time between courses of therapy administered with said antineoplastic agent and the second composition is shorter than the duration of time between courses of therapy with the antineoplastic agent alone, and further wherein toxicity of said antineoplastic agent is mitigated consequent to the administration of said antineoplastic agent.

2. The method of claim 1 wherein the second composition comprises 2,2'-dithiobis ethane sulfonate in an amount ranging from 4.1 to 41.0 g/m².

3. The method of claim 1, wherein the second composition comprises from 12.3 g/m² to 27.6 g/m² of 2,2'-dithiobis ethane sulfonate.

4. The method of claim 1, wherein the second composition comprises 18.4 g/m² of 2,2'-dithiobis ethane sulfonate.

5. The method of any of claims 1, 2, 3 or 4, wherein the 2,2'-dithiobis ethane sulfonate is a disodium salt.

6. The method of any of claims 1, 2, 3 or 4, wherein the first composition is administered prior to administration of the second composition.

7. The method of any of claims 1, 2, 3 or 4, wherein the first composition and the second composition are administered at about the same time.

8. The method of any of claims 1, 2, 3 or 4, wherein the second composition is administered both prior to and after administration of the first composition.

9. The method of any of claims 1, 2, 3 or 4, wherein the course of therapy is repeated at least once every two weeks.

10. The method of any of claims 1, 2, 3 or 4, wherein the course of therapy is repeated at least once every 1.5 weeks.

11. The method of any of claims 1, 2, 3 or 4, wherein the course of therapy is repeated at least once a week.

12. The method of any of claims 1, 2, 3 or 4, wherein the course of therapy is repeated at least twice a week.

13. The method of any of claims 1, 2, 3 or 4, wherein the course of therapy is repeated at least once per day.

14. The method of any of claims 1, 2, 3 or 4, which comprises eight or more courses of therapy.

15. The method of any of claims 1, 2, 3 or 4, which comprises nine or more courses of therapy.

16. The method of any of claims 1, 2, 3 or 4, where the duration of therapy continues for one year or more.

17. The method of any of claims 1, 2, 3 or 4, wherein the courses of therapy are completed over less than a number of weeks that is equal to the number of courses of therapy times three.

18. The method of any of claims 1, 2, 3 or 4, wherein the first composition and/or the second composition are administered intravenously.

19. The method of any of claims 1, 2, 3 or 4, wherein the antineoplastic agent is associated with neurotoxicity.

20. The method of any of claims 1, 2, 3 or 4, wherein the antineoplastic agent is a taxane antineoplastic agent.

21. The method of claim 20, wherein the taxane antineoplastic agent is paclitaxel.

22. The method of claim 20, wherein the taxane antineoplastic agent is docetaxel.

23. The method of claim 20, further comprising administering a third composition comprising a platinum analogue antineoplastic agent.

24. The method of claim 23, wherein the platinum analogue antineoplastic agent is cisplatin.

25. The method of claim 23, wherein the platinum analogue antineoplastic agent is carboplatin.

26. The method of claim 23, wherein the platinum analogue antineoplastic agent is oxaliplatin.

27. The method of any of claims 1, 2, 3 or 4, wherein the antineoplastic agent is a taxane antineoplastic agent selected from the group consisting of cephalomannine, baccatin III, and 10-deacetylbaccatin III.

28. The method of any of claims 1, 2, 3 or 4, wherein the first and/or second composition comprises a solution or suspension in liquid form, freeze-dried form or solid form.

29. The method of any of claims 1, 2, 3 or 4, wherein the antineoplastic agent and the 2,2'-dithiobis ethane sulfonate are administered in a weight ratio ranging from 1:10 to 1:2500.

30. The method of claim 1, wherein the lung cancer is non-small cell lung cancer.

31. The method of any one of claims 1, 2, 3, 4 or 4, wherein the toxicity consequent to administration of an antineoplastic agent is neurotoxicity.

32. The method of claim 31, wherein the neurotoxicity is characterized at least in part by peripheral neurotoxicity or peripheral neuropathy.

33. The method of claim 32, wherein the peripheral neurotoxicity or peripheral neuropathy is characterized at least in part by one or more of paresthesias, numbness, weakness, paralysis, arthralgia or myalgia.

34. The method of any of claims 1, 2, 3 or 4, wherein the method is carried out to shorten the duration of treatment with an antineoplastic agent.

35. The method of any of claims 1, 2, 3 or 4, wherein the method is carried out to permit an increased number of courses of therapy with the antineoplastic agent.

36. A method of mitigating neurotoxicity in a patient undergoing a treatment for breast cancer, ovarian cancer, lung cancer, bladder cancer, or adenocarcinoma, including courses of therapy with an antineoplastic agent, the method comprising administering to the patient a composition comprising from 12.3 g/m$^2$ to 27.6 g/m$^2$ of 2,2'-dithio-bis-ethane sulfonate following or at about the same time as administration of the antineoplastic agent, wherein the course of treatment is administered more frequently than once every three weeks and whereby neurotoxicity associated with administration of an antineoplastic agent is mitigated.

37. The method of claim 36, wherein the antineoplastic agent is a taxane antineoplastic agent.

38. The method of claim 37, wherein the taxane antineoplastic agent is paclitaxel or docetaxel.

39. The method of claim 36, wherein the antineoplastic agent is a platinum-based antineoplastic agent and the 2,2'-dithio-bis-ethane sulfonate is administered prior to or at about the same time as the platinum-based antineoplastic agent.

40. The method of claim 39, wherein the platinum-based antineoplastic agent is cisplatin, carboplatin or oxaliplatin.

41. The method of claim 36, wherein the neurotoxicity is characterized at least in part by peripheral neurotoxicity or neuropathy.

42. The method of claim 41, wherein the peripheral neurotoxicity or neuropathy is characterized by sensory and/or motor disorders.

43. The method of claim 42, wherein the sensory and/or motor disorder(s) are characterized by one or more of numbness in the extremities, paresthesias, weakness, paralysis, arthralgia, and/or myalgia.

44. The method of any of claim 36-42 or 43, wherein the 2,2'-dithiobis ethane sulfonate is a disodium salt.

45. A method for increasing tolerance to side effects of taxane antineoplastic agents in a patient having breast cancer, ovarian cancer, lung cancer, bladder cancer, or adenocarcinoma, by administering to the patient a composition selected from the group consisting of compositions comprising from 4.1 to 41.0 g/m$^2$ of 2,2'-dithiobis ethane sulfonate, from 12.3 g/m$^2$ to 27.6 g/m$^2$ of 2,2'-dithiobis ethane sulfonate, and comprising 18.4 g/m$^2$ of 2,2'-dithiobis ethane sulfonate prior to, after, or at about the same time as the administration of the antineoplastic agent, wherein tolerance to the side effects of the antineoplastic agent is increased.

46. A method for shortening the duration of treatment with a antineoplastic agent in a patient having breast cancer, ovarian cancer, lung cancer, bladder cancer, or adenocarcinoma, said method comprising administering to the patient a composition selected from the group consisting of compositions comprising from 4.1 to 41.0 g/m$^2$ of 2,2'-dithiobis ethane sulfonate, from 12.3 g/m$^2$ to 27.6 g/m$^2$ of 2,2'-dithiobis ethane sulfonate, and comprising 18.4 g/m$^2$ of 2,2'-dithiobis ethane sulfonate prior to or at about the same time as administration of the antineoplastic agent, whereby the duration of treatment of the patient with the antineoplastic agent is shortened.

47. The method of claims 45 or 46, wherein the taxane antineoplastic agent is paclitaxel.

48. The method of claims 45 or 46, wherein the antineoplastic agent is docetaxel.

49. The method of claims 45 or 46, wherein the antineoplastic agent is selected from the group consisting of cephalomannine, baccatin III, and 10-deacetylbaccatin III.

50. The method of claims 45 or 46, wherein the antineoplastic agent is a platinum-based antineoplastic agent.

51. A method for treating a patient having breast cancer, ovarian cancer, lung cancer, bladder cancer, or adenocarcinoma, comprising:
   administering a course of therapy to the patient comprising a first composition comprising a therapeutically effective amount of an antineoplastic agent and a composition comprising 2,2'-dithiobis ethane sulfonate in an amount selected from about 4.1, 12.3, 27.6, 18.4 and about 41.0 g/m$^2$;
   repeating the course of therapy from at least once a day to at least once every 2.5 weeks,
   wherein (a) the amount of antineoplastic agent administered in conjunction with the second composition is greater than the amount administered without the second composition and/or (b) the duration of time between courses of therapy administered with a antineoplastic agent and the second composition is shorter than the duration of time between courses of therapy with the antineoplastic agent alone.

\* \* \* \* \*